United States Patent [19]

Stoss et al.

[11] 4,294,838

[45] Oct. 13, 1981

[54] CERTAIN HETEROCYCLIC SULFOXIMIDE DERIVATIVES

[76] Inventors: Peter Stoss, Mooswaldstr. 11,, 7801 Vorstetten; Gerhard Satzinger, Im Mattenbühl 7, 7809 Denzlingen; Manfred Herrmann, Wolfweg 25, 7811 St. Peter; Wolfgang Heldt, Weidenmattenstr. 4, 7803 Emmendingen 16, all of Fed. Rep. of Germany

[21] Appl. No.: 150,119

[22] Filed: May 15, 1980

Related U.S. Application Data

[63] Continuation-in-part of Ser. No. 971,139, Dec. 19, 1978, abandoned.

[30] Foreign Application Priority Data

Dec. 29, 1977 [DE] Fed. Rep. of Germany ....... 2758613

[51] Int. Cl.$^3$ .................. A61K 31/44; C07D 213/62; C07D 407/12
[52] U.S. Cl. ............................... 424/263; 260/347.2; 546/261; 546/283; 546/284; 546/293; 549/59; 549/60; 549/65; 424/275; 424/285
[58] Field of Search .............. 546/261, 283, 284, 293; 549/59, 60, 65; 260/347.2; 424/263, 275, 285

[56] References Cited

U.S. PATENT DOCUMENTS 3,637,664  1/1972  Saltzinger et al. ........... 260/239 BA

FOREIGN PATENT DOCUMENTS 1568734  3/1974  Fed. Rep. of Germany ...... 564/102
1668146  6/1975  Fed. Rep. of Germany .. 260/239 BA

OTHER PUBLICATIONS

Index Nominum, pp. 118, 122, 150, 177, 195, 199, 220, 225, 277, 331, 588, 683, 733, 736, 739 and 839, Zurich (1979).
Chem. Abstracts, vol. 72, No. 9, item No. 43,151d, Mar. 1970 abstracting British Patent No. 1,168,700, dated 29 Oct. 1969 (9 pages).
Burger, Medicinal Chemistry, Second Edition, p. 497, Interscience Pub. (1960).

*Primary Examiner*—Alan L. Rotman
*Attorney, Agent, or Firm*—Stephen I. Miller

[57] ABSTRACT

Sulphoximide derivatives of the general formula:

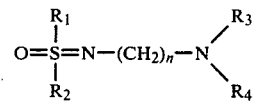

wherein $R_1$ is a phenyl, thienyl, furyl or pyridyl ring; $R_2$ is a thienyl, furyl, or pyridyl ring; $R_3$ and $R_4$ are the same or are different and are alkyl groups containing up to 6 carbon atoms or together with the nitrogen atom to which they are attached form a pyrrolidine, piperidine, or morpholine ring; and n is a whole number from 1 to 5; and the pharmaceutically acceptable organic and inorganic acid addition and quaternary ammoniuim salts thereof. The compounds of the invention exhibit antibronchospasmolytic activity.

11 Claims, No Drawings

CERTAIN HETEROCYCLIC SULFOXIMIDE DERIVATIVES

CROSS REFERENCE TO RELATED APPLICATION

This application is a continuation-in-part of our copending application Ser. No. 971,139, filed Dec. 19, 1978 now abandoned.

SUMMARY OF THE INVENTION

The present invention relates to sulphoximide derivatives of the formula:

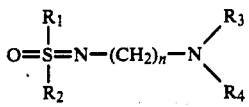

wherein $R_1$ is a phenyl, thienyl, furyl or pyridyl ring; $R_2$ is a thienyl, furyl or pyridyl ring; $R_3$ and $R_4$, which can be the same or different, are alkyl groups containing up to 6 carbon atoms or $R_3$ and $R_4$, together with the nitrogen atom to which they are attached, can form a pyrrolidine, piperidine or morpholine ring and n is a whole number of from 1 to 5; and the pharmaceutically acceptable salts thereof with organic and inorganic acids, as well as the quaternary ammonium salts thereof.

The present invention also relates to a process for the preparation of sulphoximide derivatives of the formula:

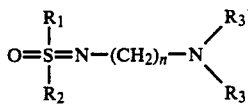

wherein $R_1$ is a phenyl, thienyl, furyl or pyridyl ring; $R_2$ is a thienyl, furyl or pyridyl ring; $R_3$ and $R_4$, which can be the same or different, are alkyl groups containing up to 6 carbon atoms or $R_3$ and $R_4$, together with the nitrogen atom to which they are attached, can form a pyrrolidine, piperidine or morpholine ring and n is a whole number of from 1 to 5; wherein a sulphoximide of the general formula:

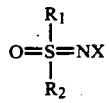

in which $R_1$ and $R_2$ are as defined above and X is an alkali metal atom, is reacted with a compound of the formula:

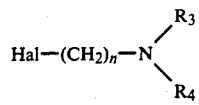

in which $R_3$, $R_4$ and n are as defined above and Hal is chlorine, bromine or iodine.

The present invention also relates to a pharmaceutical composition, comprising at least one sulphoximide derivative of the formula:

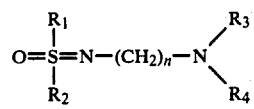

wherein $R_1$, $R_2$, $R_3$, $R_4$ and n are as defined above; in admixture with a solid or liquid pharmaceutical diluent or carrier.

DESCRIPTION OF THE INVENTION

Pharmaceutically interesting N-(dialkylaminoalkyl)-S,S-diphenylsulphoximides and the salts thereof are known from German Pat. Nos. 1,568,734 and 1,668,146 and U.S. Pat. No. 3,637,664.

We have now found that sulphoximides in which either or both of the S-phenyl substituents are replaced by heterocyclic rings are characterised by advantageous pharmacological properties in comparison with the above-mentioned previously described compounds.

Thus, according to the present invention, there are provided sulphoximide derivatives of the formula:

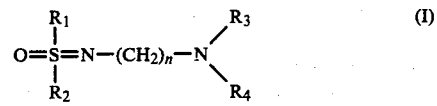

wherein $R_1$ is a phenyl, thienyl, furyl or pyridyl ring; $R_2$ is a thienyl, furyl or pyridyl ring; $R_3$ and $R_4$, which can be the same or different, are alkyl groups containing up to 6 carbon atoms, or together with the nitrogen atom to which they are attached, may form a pyrrolidine, piperidine or morpholine ring and n is a whole number of from 1 to 5; and the pharmaceutically acceptable salts thereof with organic and inorganic acids, as well as the quaternary ammonium salts thereof.

According to the present invention, the alkyl groups which can be straight- or branched-chain, may contain up to 6 and preferably up to 3 carbon atoms.

The new compounds (I) according to the present invention can be prepared, for example, by reacting a sulphoximide of the formula:

in which $R_1$ and $R_2$ have the same meanings as above and X is an alkali metal atom, with a compound of the formula:

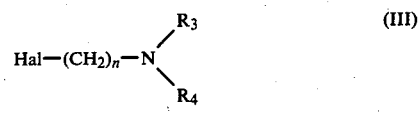

in which $R_3$, $R_4$ and n have the same meanings as above and Hal is chlorine, bromine or iodine, or with a salt thereof and subsequently, if desired, the product obtained is converted into a pharmacologically acceptable salt by reaction with an organic or inorganic acid or is converted into a quaternary ammonium salt by reaction of the amine nitrogen atom with a lower alkyl halide or dialkyl sulphate.

The quaternary ammonium salts are compounds of the general formula:

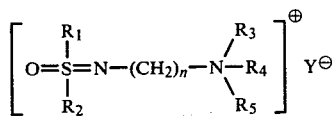

in which $R_1$, $R_2$, $R_3$, $R_4$ and n have the same meanings as above, $R_5$ is a lower alkyl radical and $Y^\ominus$ is a halide ion or an alkyl sulphate ion.

The dialkyl sulphates contemplated by the invention are lower dialkyl sulphates, especially dimethyl sulphate or diethyl sulphate.

The compounds of formula (II) can be prepared by reacting a compound of the general formula:

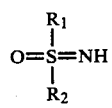

in which $R_1$ and $R_2$ have the same meanings as above, with an alkali metal, alkali metal hydride, alkali metal hydroxide, alkali metal carbonate or organic alkali metal compound, for example n-butyl lithium, in an appropriate solvent, for example benzene, toluene, xylene, dioxane, tetrahydrofuran, acetone, methyl ethyl ketone, dimethyl formamide or dimethyl sulphoxide at a temperature within the range of from 20° to 150° C. For practical reasons, it is preferable to work at ambient temperature or at the boiling temperature of the solvent.

The reaction of the sulphoximide alkali metal salts of general formula (II) with compounds of formula (III) or salts thereof is preferably also carried out in one of the above-mentioned solvents and preferably at the boiling point of the solvent used. The reaction time is in the range of from 1 to 6 hours.

The compounds thus obtained of formula (I) can be isolated in any appropriate manner and, if desired, converted by reaction with appropriate acids into physiologically compatible salts, for example, hydrochlorides, hydrobromides, hydroiodides, phosphates, sulphates, nitrates, acetates, oxalates, fumarates, maleates, citrates, benzenesulphonates, toluenesulphonates or naphthalenesulphonates, or they may be converted into quaternary ammonium salts of general formula (IV).

The new compounds according to the present invention show outstanding polyvalent spasmolytic effects after oral or parenteral administration to warm blooded animals. Furthermore, the compounds possess an outstanding peripheral anti-tussive action.

The compounds of the present invention were evaluated for their pharmacological activities according to the following standard test procedures:

Acute Toxicity

The acute toxicity has been determined in male mice (NRMI strain) weighing 17 to 21 g. The animals were fasted 24 hours prior to the trial. Water was offered ad libidum. The substances were administered subcutaneously and by using a gastric tube in increasing doses to groups consisting of 6 animals. The animals were observed over a period of 24 hours. The $LD_{50}$ values were determined according to the method of Litchfield and Wilcoxon (Therap. Grundlagen der experimentellen Arzneimittelforschung—Ther. Fundamentals of Experimental Durg Research—1965—page 82). The findings were compiled as average values in the following tables:

TABLE I

| | Acute Toxicity | |
|---|---|---|
| Example | S.C. | w.i.g. |
| 4 | 150 | 200 |
| 1 | 150 | 200 |
| 5 | 100 | 250 |
| 8 | 250 | <300 |
| 9 | 30 | >30 |
| 12 | — | 1.600 |
| 10 | 150 | 400 |
| 6 | — | 200 |
| 7 | — | 1.000 |
| 2 | 600 | <800 |
| 2* | 300 | >400 |
| 3 | — | 150 |
| ** | 175 | 180 |

*(Trimethylammonium-iodide)
**Sulfoxifen-Phosphate
Sulfoxifen: N-(2-Diethylaminoethyl)-diphenyl-sulfoximin U.S. Pat. No. 3,637,664

Bronchospasmolytic activity

The method described by Konzett and Roessler was employed (Arch.exp.Path.Pharmak. 195, 72 (1940).

Experimental animals were guinea pigs weighing between 280 and 380 g. The animals were kept under urethane narcosis (1.5 g/kg i.m.) and their chests opened. The animals received artificial respiration by means of a respiratory pump. The respiratory pressure was adjusted by a mercury manometer. Every 4 minutes a bronchospasm was caused by intravenous application (vena jugularis) of spasmodics. These were acetylcholine and histamine. Two minutes prior to the injection of a spasmodic, the substances under investigation were administered, i.e. again by intravenous injection. The following Tabe II shows that the compounds are effective with respect to the acetylcholine-spasm in the range of 1 to 4 mg. With respect to the histamine-spasm they were active in the range of 4 to 8 mg.

TABLE II

| | Bronchospasmolytic Activity | |
|---|---|---|
| | $ED_{100}$ - mg/kg | |
| Example | Acetyl-choline | Histamine |
| 4 | >2 | >8 |
| 1 | 1 | >4 |
| 5 | 2 | >8 |
| 8 | 2 | 4 |
| 9 | 4 | >8 |
| Sulfoxifen-Phosphate | 4 | 4 |

Spasmolytic Activity

The method described by Magnus was employed [Therap. Grundlagen der Experimentellen Arzneimittelforschung, Wiss. Verlagsgesellschaft, Stuttgart (1965) page 241].

Guinea pigs of both sexes weighing between 200 and 500 g were killed by cervical blow. After that they were allowed to bleed and then laparotomized. About 15 cm of the distal ileum were then placed into a Krebs-Henseleit-solution at 37° C.

Ileum preparations of about 1 cm length were fixed in a special vessel containing 25 ml of the Krebs-Henseleit solution which were percolated by a gas mixture (Carbogen) consisting of 95% oxygen and 5% carbon dioxide. The temperature of the bath was maintained at 37

C. The movements of the ileum preparations were observed by a lampblack-kymograph.

Every 10 minutes single spasms were caused with solutions of acetylcholine ($4 \times 10^{-7}$ g/ml) barium chloride ($4 \times 10^{-4}$ g/ml) and histamine ($8 \times 10^{-6}$ g/ml) in the Krebs-Henseleit-solution. Five minutes after application the spasms were stopped by rinsing the ileum segments with a Krebs-Henseleit-solution which was free of spasmodics. The tested compounds were added to ther Krebs-Henseleit-solution 2 minutes after causing the spasms.

The $ED_{50}$ values determined by the described Magnus-method are shown in the following Table III:

TABLE III

| | Spasmolytic Activity $ED^{50}$ - g/ml | | |
|---|---|---|---|
| Example | Acetylcholine | Barium-Chloride | Histamine |
| 4 | $1 \times 10^{-6}$ | $4 \times 10^{-5}$ | $1 \times 10^{-5}$ |
| 1 | $1 \times 10^{-6}$ | $8 \times 10^{-5}$ | $5 \times 10^{-6}$ |
| 5 | $1 \times 10^{-6}$ | $4 \times 10^{-5}$ | $1 \times 10^{-5}$ |
| 8 | $5 \times 10^{-7}$ | $8 \times 10^{-5}$ | $2 \times 10^{-6}$ |
| 9 | $2,5 \times 10^{-7}$ | — | $1 \times 10^{-5}$ |
| 6 | $5 \times 10^{-6}$ | $8 \times 10^{-5}$ | $1 \times 10^{-5}$ |
| 7 | $4 \times 10^{-6}$ | — | $4 \times 10^{-5}$ |
| 2 | $> 10^{-6}$ | $> 10^{-5}$ | $5 \times 10^{-5}$ |
| 2* | $5 \times 10^{-6}$ | — | — |
| 3 | $> 10^{-6}$ | — | $5 \times 10^{-6}$ |
| Suloxifen-phosphatre | $1 \times 10^{-7}$ | $4 \times 10^{-5}$ | $1 \times 10^{-6}$ |
| | $[1 \times 10^{-6}$ (ED$_{100}$)] | $[8 \times 10^{-5}$ (ED$_{100}$)] | $[1 \times 10^{-5}$ (ED$_{100}$)] |

*Trimethylammonium-iodide

The present invention also provides pharmaceutical compositions comprising an effective amount of at least one of the new compounds according to the present invention, in admixture with a solid or liquid pharmaceutical diluent or carrier. Such compositions include, for example, tablets, capsules, dragees, drops, suppositories and injection solutions. Administration can be orally, rectally or by injection.

The dosage range for the compounds of the invention will vary with the particular composition being employed, the route of administration, the severity of the symptoms and the animal being treated. In general, by the oral route, the single dose is from 5–60 mg and from 20–40 mg is preferred; parenterally the single dose is from 1–50 mg and 5–30 mg is preferred. Single doses may be given 1 to 3 times a day to grown up persons.

The following Examples are given for the purpose of illustrating the present invention:

EXAMPLE 1

N-(2-Diethylaminoethyl-S-phenyl-S-(2-thienyl)-sulphoximide

Stage 1

Phenyl-(2-thienyl)-sulphimide mesitylene-sulphonate 65 g. O-Mesityl-sulphonyl-hydroxylamine are dissolved in 500 ml. dichloromethane and added dropwise to a solution of 40 g. phenyl-(2-thienyl)-sulphide in 500 ml. dichloromethane. The reaction mixture is stirred for 20 hours at ambient temperature, then mixed with petroleum ether and the resultant precipitate is filtered off with suction. After recrystallisation from isopropanol, there are obtained 61 g. phenyl-(2-thienyl)-sulphimide mesitylene-sulphonate; m.p. 125° C.

Stage 2

Phenyl-(2-thienyl)-sulphoximide 10 g. Phenyl-(2-thienyl)-sulphimide mesitylene-sulphonate are dissolved in 200 ml. methanol. A solution of 7 g. sodium periodate in 150 ml. water are added dropwise thereto, whereafter the reaction mixture is stirred for 24 hours at ambient temperature. The reaction mixture is then rendered alkaline and evaporated on a rotary evaporator. The residue obtained is partitioned between water and dichloromethane and the organic phase is evaporated. There are obtained 3.7 g. phenyl-(2-thienyl)-sulphoximide which, after recrystallisation from ethyl acetate/isopropanol, melts at 133° C.

Stage 3

N-(2-Diethylaminoethyl)-S-phenyl-S-(2-thienyl)-sulphoximide 6 g. of an 80% sodium hydride-mineral oil suspension are added portionwise to a solution of 24 g. phenyl-(2-thienyl)-sulphoximide in 1 liter anhydrous dioxane and the reaction mixture then boiled under reflux for 2 horus. Thereafter, the reaction mixture is mixed with 36 g. 2-diethylaminoethyl chloride and reflux boiling continued for a further 5 hours. After removing the solvent in a vacuum, the residue is mixed with water and extracted with dichloromethane and the extract is dried and evaporated. There are obtained 30.1 g. N-(2-diethylaminoethyl)-S-phenyl-S-(2-thienyl)-sulphoximide from which, by reaction with fumaric acid in ethyl acetate, there is prepared the corresponding fumarate which, after recrystallisation from ethyl acetate/iospropanol, melts at 116° C.

EXAMPLE 2

N-(3-Dimethylaminopropyl)-S-phenyl-S-(2-thienyl)-sulphoximide and the trimethyl ammonium iodide thereof In a manner analogous to that described in Example 1, Stage 3, by the reaction of phenyl-(2-thienyl)-sulphoximide with 3-dimethylaminopropyl chloride, there is obtained, in a yield of 38% of theory, N-(3-dimethylaminopropyl)-S-phenyl-S-(2-thienyl)-sulphoximide, the fumarate of which, after recrystallisation from ethyl acetate/isopropanol, melts at 125° C.

For conversion into the corresponding trimethyl ammonium iodide, the base is dissolved in nitromethane, mixed with a molar amount of methyl iodide and stirred for 2 hours at ambient temperature. The reaction mixture is then evaporated and the residue recrystallised from ethanol. There is obtained N-(3-trimethyl ammonium propyl)-S-phenyl-S-(2-thienyl)-sulphoximide iodide in a yield of 70% of theory; m.p. 154° C.

EXAMPLE 3

N-(2-Pyrrolidinoethyl)-S-phenyl-S-(2-thienyl)-sulphoximide

In a manner analogous to that described in Example 1, Stage 3, from phenyl-(2-thienyl)-sulphoximide, there is obtained, by reaction with 2-pyrrolidinoethyl chloride, N-(2-pyrrolidinoethyl)-S-phenyl-S-(2-thienyl)-sulphoximide in a yield of 65% of theory. After recrystallisation from diisopropyl ether, the compound melts at 82° C.

EXAMPLE 4

N-(2-Diethylaminoethyl)-S-phenyl-S-(3-thienyl)-sulphoximide

Stage 1

Phenyl-(3-thienyl)-sulphimide mesitylene-sulphonate

In a manner analogous to that described in Example 1, Stage 1, from phenyl-(3-thienyl)-sulphide and O-mesitylsulphonyl-hydroxylamine in dichloromethane, there is obtained phenyl-(3-thienyl)-sulphimide mesitylene-sulphonate in a yield of 65% in theory; after recrystallisation from isopropanol, the compound melts at 116° C.

Stage 2

Phenyl-(3-thienyl)-sulphoximide

In a manner analogous to that described in Example 1, Stage 2, from phenyl-(3-thienyl)-sulphimide mesitylenesulphonate, there is obtained, by oxidation with sodium periodate, phenyl-(3-thienyl)-sulphoximide in a yield of 85% of theory; after recrystallisation from diiosopropyl ether/ethyl acetate, the compound melts at 100° C.

Stage 3

N-(2-Diethylaminoethyl)-S-phenyl-S-(3-thienyl)-sulphoximide

In a manner analogus to that described in Example 1, Stage 3, from phenyl-(3-thienyl)-sulphoximide and 2-diethylaminoethyl chloride, there is obtained N-(2-diethylaminoethyl)-S-phenyl-S-(3-thienyl)-sulphoximide fumarate in a yield of 60% of theory; after recrystallisation from ethyl acetate/isopropanol, the compound melts at 115° C.

EXAMPLE 5

N-(2-Diethylaminoethyl)-S,S-bis-(2-thienyl)-sulphoximide

Stage 1

2,2'-Dithienyl-sulphimide mesitylene-sulphonate

In a manner analogous to that described in Example 1, Stage 1, from 2,2'-dithienyl sulphide and O-mesitylsulponylhydroxylamine, there is obtained 2,2'-dithienyl-sulphimide mesitylene-sulphonate in a yield of 78% of theory; after recrystallisation from isopropanol, the compound melts at 134° C.

Stage 2

2,2'-Dithienyl-sulphoximide

In a manner analogous to that described in Example 1, Stage 2, from 2,2'dithienyl-sulphimide mesitylene-sulphonate there is obtained, by oxidation with sodium periodate, 2,2'-dithienyl-sulphoximide in a yield of 96% of theory; after recrystallisation from ethyl acetate, the compound melts at 168° C.

Stage 3

N-(2-Diethylaminoethyl)-S,S-bis-(2-thienyl)-sulphoximide

In a manner analogous to that described in Example 1, Stage 3, from 2,2'-dithienyl-sulphoximide and 2-diethylaminoethyl chloride, there is obtained N-(2-diethylaminoethyl)-S,S-bis-(2-thienyl)-sulphoximide in a yield of 67% of theory. The fumarate, after recrystallisation from isopropanol, melts at 131° C.

EXAMPLE 6

N-(2-Piperidinoethyl)-S,S-bis-(2-thienyl)-sulphoximide

In a manner analogous to that described in Example 1, Stage 3, from 2,2'-dithienyl-sulphoximide and 2-piperidinoethyl chloride, there is obtained N-(2-piperidinoethyl)-S,S-bis-(2-thienyl)-sulphoximide in a yield of 42% of theory; after recrystallisation from diiosopropyl ether, the compound melts at 81° C.

EXAMPLE 7

N-(2-Morpholinoethyl)-S,S-bis-(2-thienyl)-sulphoximide

In a manner analogous to that described in Example 1, Stage 3, from 2,2'dithienyl-sulphoximide and 2-morpholinoethyl chloride, there is obtained N-(2-morpholinoethyl)-S,S-bis-(2-thienyl)-sulphoximide in a yield of 46% of theory. The fumarate, after recrystallisation from isopropanol, melts at 190° C.

EXAMPLE 8

N-(2-Diethylaminoethyl)-S-(2-thienyl)-S-(3-thienyl)-sulphoximide

Stage 1

2,3'-Dithienyl-sulphimide mesitylene sulphonate

In a manner analogous to that described in Example 1, Stage 1, from 2,3'-dithienyl sulphide and O-mesitylsulphonyl-hydroxylamine, there is obtained 2,3'-dithienyl-sulphimide mesitylene-sulphonate in a yield of 71% of theory; after recrystallisation from isopropanol, the compounds melt at 114° C.

Stage 2

2,3'-Dithienyl sulphoximide

In a manner analogous to that described in Example 1, Stage 2, from 2,3'-dithienyl-sulphimide mesitylene-sulphonate there is obtained, by oxidation with sodium periodate, 2,3'-dithienyl-sulphoximide in a yield of 89% of theory; after recrystallisation from ethyl acetate, the compound melts at 152° C.

Stage 3

N-(2-Diethylaminoethyl)-S-(2-thienyl)-S-(3-thienyl)-sulphoximide

In a manner analogous to that described in Example 1, Stage 3, from 2,3'-dithienyl-sulphoximide and 2-diethylaminoethyl chloride, there is obtained N-(2-diethylaminoethyl)-S-(2-thienyl)-S-(3-thienyl)-sulphoximide in a yield of 53% of theory; after recrystallisation from isopropanol, the compound melts at 126°–127° C.

EXAMPLE 9

N-(2-Diethylaminoethyl)-S,S-bis-(bis-(3-thienyl)-sulphoximide

Stage 1

3,3'-Dithienyl-sulphimide mesitylene-sulphonate

In a manner analogous to that described in Example 1, Stage 1, from 3,3'-dithienyl-sulphide and O-mesitylsulphonyl-hydroxylamine, there is obtained 3,3'-dithienyl-sulphimide-mesitylene-sulphonate in a yield of 79% of theory; after recrystallisation from isopropanol, the compound melts at 125° C.

Stage 2

3,3'-Dithienyl-sulphoximide

In a manner analogous to that described in Example 1, Stage 2, from 3,3'-dithienyl-sulphimide mesitylene-sulphonate, there is obtained, by oxidation with sodium periodate, 3,3'-dithienyl-sulphoximide is a yield of 87% of theory. After recrystallisation from ethyl acetate, the compound melts at 142° C.

Stage 3

N-(2-Diethylaminoethyl)-S,S-bis-(3-thienyl)-sulphoximide

In a manner analogous to that described in Example 1, Stage 3, from 3,3'-dithienyl-sulphoximide and 2-diethylaminoethyl chloride, there is obtained N-(2-diethylaminoethyl)-S,S-bis-(3-thienyl)9-sulphoximide in a yield of 46% of theory; the corresponding fumarate has a melting point of 116° C.

EXAMPLE 10

N-(2-Diethylaminoethyl)-S-(2-furyl)-S-phenyl-sulphoximide

Stage 1

(2-Furyl)-phenyl-sulphimide mesitylene-sulphonate

In a manner analogous to that described in Example 1, Stage 1, from (2-furyl)-phenyl sulphide and O-mesityl-sulphonyl-hydroxylamine, there is obtained (2-furyl)-phenyl-sulphimide mesitylene-sulphonate in a yield of 95% of theory. The substance is obtained in the form of oil.

Stage 2

S-(2-Furyl)-S-phenyl-sulphoximide

In a manner analogous to that described in Example 1, Stage 2, from (2-furyl)-phenyl-sulphimide mesitylene-sulphonate there is obtained, by oxidation with sodium periodate, S-(2-furyl)-S-phenyl-sulphoximide in a yield of 52% of theory. After recrystallisation from diisopropyl ether and ethyl acetate, the compound has a melting point of 122° C.

Stage 3

N-(2-Diethylaminoethyl)-S-(2-furyl)-S-phenyl-sulphoximide

In a manner analogous to that described in Example 1, Stage 3, from S-(2-furyl)-S-phenyl-sulphoximide and 2-diethylaminoethyl chloride, there is obtained N-(2-diethylaminoethyl-S-(2-furyl)-S-phenyl-sulphoximide in a yield of 48% of theory. The corresponding fumarate, after recrystallisation from ethyl acetate/isopropanol, melts at 133° C.

EXAMPLE 11

N-(Piperidinomethyl)-S-(2-furyl)-S-phenyl-sulphoximide

A suspension of the sodium salt of S-(2-furyl)-S-phenyl-sulphoximide is stirred with a molar amount of N-piperidino-methylene-iminium chloride in anhydrous benzene for 3 hours at 50° C. The reacton mixture is then filtered and freed from benzene in a vacuum. There is obtained, in a yield of 85% of theory, N-(piperidinomethyl-S-(2-furyl)-S-phenyl-sulphoximide in the form of a pale yellowish oil.

EXAMPLE 12

N-(2-Diethylaminoethyl)-S-phenyl-S-(3-pyridyl)-sulphoximide

Stage 1

3-(Phenyl-sulphinyl)-pyridine 23.6 g. 35% perhydrol is added dropwise to a solution of 44 g. 3-phenylthiopryidine in 200 ml. glacial acetic acid. The reaction mixture is stirred for 24 hours at ambient temperature and then poured into ice water. The mixture is rendered alkaline by adding aqueous ammonia, while cooling, and then extracted with dichloromethane. The extract is dried and evaporated and the residue is recrystallised from diisopropyl ether/ethyl acetate. There is obtained 3-(phenyl-sulphinyl)-pyridine in a yield of 83% of theory; m.p. 56° C.

Stage 2

S-Phenyl-S-(3-pyridyl)-sulphoximide

A mixture of 15 g. 3-(phenyul-sulphinyl)-pyridine, 350 ml. 85% phosphoric acid and 210 g. phosphorous pentoxide is heated at 100° C. 14 g. sodium azide are introduced portion-wise at this temperature, while stirring, and the reaction mixture is thereafter stirred for 20 hours at 100° C. Then, while cooling efficiently, the reaction mixture is mixed with water, rendered alkaline with potassium hydroxide and extracted with dichloromethane. The residue obtained after evaporating the dichloromethane phase is recrystallised from ethyl acetate. There are obtained 15 g. S-phenyl-S-(3-pyridyl)-sulphoximide; m.p. 109° C.

Stage 3

N-(2-Diethylaminoethyl)-S-phenyl-S-(3-pyridyl)-sulphoximide

In a manner analogous to that described in Example 1, Stage 3, from S-phenyl-S-(3-pyridyl)-sulphoximide and 2-diethylaminoethyl chloride, there is obtained, in a yield of 46% of theory, N-(2-diethylaminoethyl)-S-phenyl-S-(3-pyridyl)-sulphoximide. The corresponding dibenzoyltartrate, after recrystallisation from isoporopanol, melts at 130° C.

We claim:

1. Sulphoximide derivatives of the general formula:

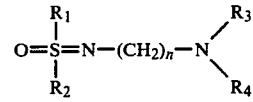

wherein $R_1$ is a phenyl, thienyl, furyl or pyridyl ring; $R_2$ is a thienyl, furyl or pyridyl ring; $R_3$ and $R_4$, which can be the same or different, are alkyl groups containing up to 6 carbon atoms and n is a whole number of from 1 to 5; and the pharmaceutically acceptable salts thereof with organic and inorganic acids, as well as the pharmaceutically acceptable quaternary ammonium salts thereof.

2. Sulphoximide derivatives according to claim 1, wherein $R_3$ and $R_4$ are methyl or ethyl; n is a whole number of from 1 to 3; and the pharmaceutically acceptable salts thereof with organic and inorganic acids, as well as the pharmaceutically acceptable quaternary ammonium salts thereof.

3. The compound defined in claim 1 which is N-(2-Diethylaminoethyl)-S-phenyl-S-(2-thienyl)-sulphoximide and the pharmaceutically acceptable fumarate salt thereof.

4. The compound defined in claim 1 which is N-(3-Dimethylaminopropyl)-S-phenyl-S-(2-thienyl)-sulphoximide and the trimethyl ammonium iodide thereof.

5. The compound defined in claim 1 which is N-(2-diethylaminoethyl)-S-phenyl-S-(3-thienyl)-sulphoximide and the pharmaceutically acceptable fumarate salt thereof.

6. The compound defined in claim 1 which is N-(2-diethylaminoethyl)-S,S-bis-(2-thienyl)-sulphoximide and the pharmaceutically acceptable fumarate salt thereof.

7. The compound defined in claim 1 which is N-(2-diethylaminoethyl)-S-(2-thienyl)-S-(3-thienyl)-sulphoximide and the pharmaceutically acceptable fumarate salt thereof.

8. The compound defined in claim 1 which is N-(2-diethylaminoethyl)-S,S-bis(3-thienyl)-sulphoximide and the pharmaceutically acceptable fumarate salt thereof.

9. The compound defined in claim 1 which is N-(2-diethylaminoethyl)-S-(2-furyl)-S-phenyl-sulphoximide and the pharmaceutically acceptable fumarate salt thereof.

10. The compound defined in claim 1 which is N-(2-diethylaminoethyl)-S-phenyl-S-(3-pyridyl)-sulphoximide and the pharmaceutically acceptable dibenzoyltartrate salt thereof.

11. An anti-spasmodic composition, comprising a sulphoximide derivative according to claim 1, in admixture with an inert solid or liquid pharmaceutical diluent or carrier.

* * * * *